US00PP31732P2

(12) United States Plant Patent
Hansen

(10) Patent No.: US PP31,732 P2
(45) Date of Patent: May 5, 2020

(54) ***PHLOX* PLANT NAMED 'OPENING ACT PINK-A-DOT'**

(50) Latin Name: ***Phlox* hybrid**
Varietal Denomination: Opening Act Pink-a-Dot

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/602,097

(22) Filed: Aug. 6, 2019

(51) Int. Cl.
*A01H 5/02* (2018.01)
*A01H 6/70* (2018.01)

(52) U.S. Cl.
USPC ..... Plt./320

(58) Field of Classification Search
USPC ..... Plt./320
CPC ..... A01H 5/02; A01H 6/70
See application file for complete search history.

*Primary Examiner* — Annette H Para

(57) ABSTRACT

A new and unique hybrid cultivar of garden *phlox* named *Phlox* 'Opening Act Pink-a-Dot' multi-stemmed, medium upright height, slowly-spreading habit with clean, medium-green, glossy, lanceolate leaves with exceptional powdery mildew resistance. Foliage is thick and leathery on stiff stems. Flowers are near white with deep pink eye resembling a star, produced on branched peduncles and nearly cover the top of the plant beginning early summer, about two weeks prior typical *Phlox paniculata* cultivars and continuing for about five weeks. 'Opening Act Pink-a-Dot' is especially suitable as a potted plant, for the garden, for attracting hummingbirds and butterflies, and for cut flower arrangements.

1 Drawing Sheet

Botanical classification: *Phlox* hybrid.
Variety denomination: 'Opening Act Pink-a-Dot'.

STATEMENT REGARDING PRIOR DISCLOSURES UNDER 37 CFR 1.77(B)(6)

The first disclosure, in the form of a sale, was made by Walters Gardens, Inc. on Aug. 6, 2018 to Prides Corner. Subsequently, Walters Gardens, Inc. also sold the new plant to Overdevest Nursery on Aug. 20, 2018 and to Bell Nursery on Sep. 24, 2018. Walters Gardens, Inc. obtained the new plant and all information relating thereto, from the inventor. No plants of *Phlox* 'Opening Act Pink-a-Dot' have been sold, in this country or anywhere in the world, nor has any disclosure of the new plant been made, more than one year prior the filing date of this application, and such sale or disclosure within one year was either derived directly or indirectly from the inventor.

BACKGROUND OF THE INVENTION

The present invention relates to a new and distinct hybrid cultivar of *Phlox* plant, known as *Phlox* 'Opening Act Pink-a-Dot' and will be referred to hereafter by its cultivar name or the "new plant". The new plant was the result of a cross pollination of 'Amethyst Pearl' U.S. Plant Pat. No. 28,487 as the female or seed parent and *Phlox carolina* 'Lil' Cahaba' (not patented) as the male or pollen parent. The cross was performed by the inventor on Nov. 17, 2013 in the greenhouses at a wholesale perennial nursery in Zeeland, Mich., and seed was collected in the early winter of 2014. During the trial process the new plant was identified by the breeder code 14-24-1. 'Opening Act Pink-a-Dot' has been asexually propagated by tip and basal stem cuttings in the greenhouses at the same nursery in Zeeland, Mich. since 2016, as well as by shoot tip tissue culture. The unique characteristics of the new plant have been found to be reproducible and stable in successive generations of asexually propagated plants and the resultant plants have been found to be identical to the original selection.

BRIEF SUMMARY OF THE PLANT

*Phlox* 'Opening Act Pink-a-Dot' is unique from its parents and all other tall garden *phlox* or other hybrid *Phlox* known to the inventor. The new plant differs from the female parent in that the female parent is shorter and has light amethyst-pink-colored flowers. The male parent, 'Lil' Cahaba' is slightly taller and has flowers of pinky-mauve without the lighter face surrounding the darker eye. 'Kung Fuchsia' U.S. Plant Pat. No. 31,308 is slightly shorter in habit and has bright fuchsia flower faces with light pink eye zones markings. The most closely comparison cultivars known to the inventor are *Phlox* 'Cloudburst' U.S. Plant Pat. No. 30,289, 'Kung Fuchsia' U.S. Plant Pat. No. 31,308, 'Baby Doll Pink' U.S. Plant Patent Application copending; 'Opening Act Blush' U.S. Plant Pat. No. 27,462, 'Opening Act White' U.S. Plant Pat. No. 27,461, 'Forever Pink' U.S. Plant Pat. No. 24,918 and 'Fashionably Early Crystal' U.S. Plant Pat. No. 28,679. 'Cloudburst' is slightly taller in habit and has more lavender purple flowers with smaller bright pink eyes. 'Kung Fuchsia' U.S. Plant Pat. No. 31,308 is slightly shorter in habit and has bright fuchsia flower faces with light pink eye zones markings. 'Baby Doll Pink' has a shorter habit with flowers of darker pink and a white eye. 'Opening Act Blush' has a slightly shorter habit with smaller, light lavender-pink flowers. 'Opening Act White' has a slightly shorter habit with white flowers without a pink eye. 'Forever Pink' has a shorter flower season smaller, darker pink flowers, and the habit is shorter. 'Fashionably Early Crystal' has taller and broader habit with larger foliage and larger inflorescence and the flower lacks the large pink eye. 'Fashionably Early Princess' U.S. Plant Pat. No. 28,680 has fragrant flowers of light fuchsia-pink with a darker eye on taller plants. 'Fashionably Early Lavender Ice' U.S. Plant Pat. No. 29,912 has a taller habit and the flowers are pale lavender with a smaller lavender-pink eye. 'Opening Act Pink-a-Dot' differs from all other *phlox* known to the inventor in the following repeatedly observed traits in combination:

1. Plants of medium upright habit, slowly spreading by short rhizomes, producing clean, leathery, glossy, medium-green, lanceolate leaves;
2. Showing exceptional powdery mildew resistance;
3. Multiple branched, stems produce branched mounds of flowers starting early in the season;
4. Flower on strong stiff stems of about 66.0 cm tall producing pale pink to near white flower faces with large deep pink eye markings resembling star;
5. Flowers cover nearly the entire top of the plant;
6. Flowering beginning in early-summer about two weeks prior to typical *Phlox paniculata* cultivars and re-blooming through late-summer.

BRIEF DESCRIPTION OF THE DRAWINGS

The photographs of the new plant demonstrate the unique traits of 'Opening Act Pink-a-Dot' and the overall appearance of the plant at two-years-old grown in a full sun trial garden in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
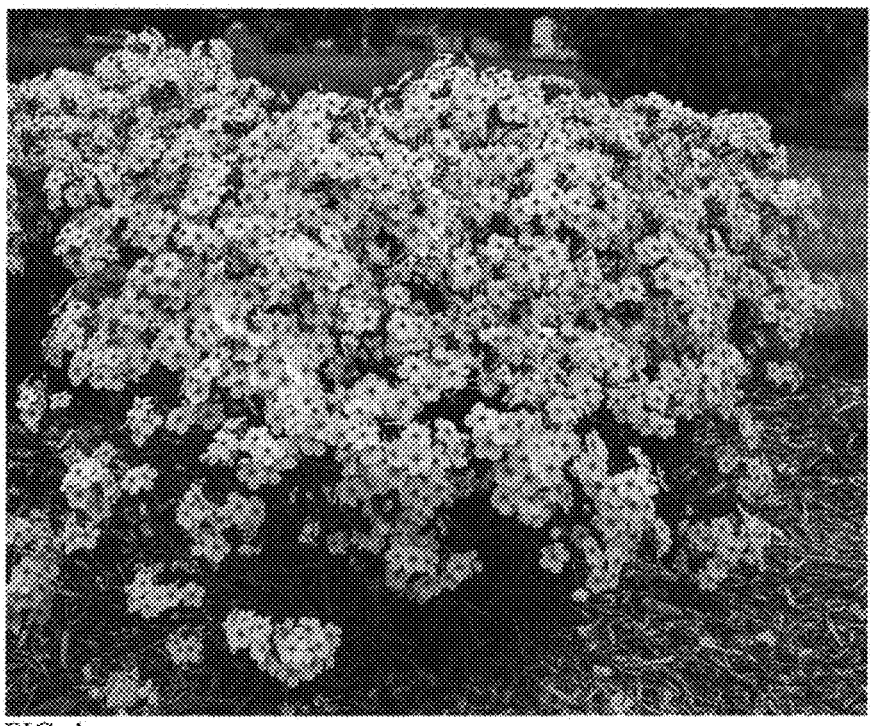
FIG. 1 shows the new plant in peak flower in the landscape.
Figure 2:
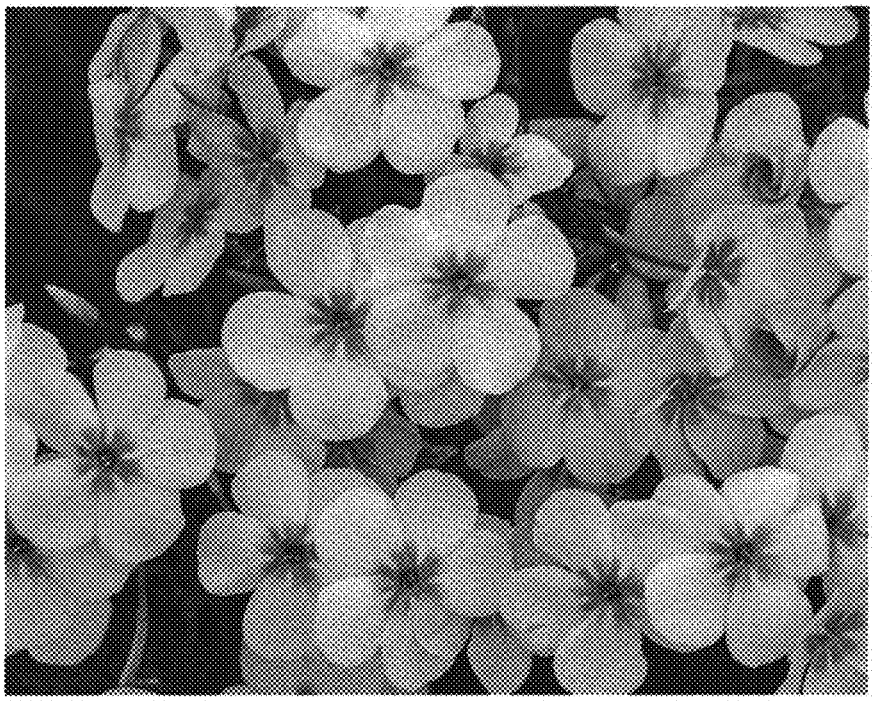
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Opening Act Pink-a-Dot' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun garden of a wholesale perennial nursery in Zeeland, Mich. with supplemental fertilizer and water as needed.

Botanical classification: *Phlox* hybrid;

Parentage: Female or seed parent 'Amethyst Pearl' male or pollen parent *Phlox carolina* 'Lil' Cahaba';

Plant habit: Hardy herbaceous perennial, densely upright, producing about 30 rigid mostly upright stems; flowering about 66.0 cm tall and about 65.0 cm wide; flowering begins early summer in Michigan and continuing for about 5 weeks;

Propagation: Stem cuttings; rooting in about 14 days;

Time to produce finished crop in 3.8 liter pots: About 8 to 10 weeks; moderate rate of growth;

Root: Primary roots to about 1.0 mm thick; secondary fibrous and freely branching; color creamy white to tan depending on soil type;

Leaves: Simple, opposite, lanceolate, tough; narrowly acute apex; rounded to attenuate base; entire margin with micro-ciliolate in basal margin portion;

Leaf size: To about 16.0 cm long by about 25.0 mm wide, average about 12.0 cm long by about 17.0 mm wide;

Leaf surfaces: Glabrous and lustrous adaxial and glabrous and matte adaxial;

Leaf color expanding: Abaxial between RHS 146B and RHS 138A, adaxial nearest RHS 144A;

Leaf color at flowering: Abaxial between RHS 138A and RHS 146B, adaxial nearest RHS 137A;

Foliage fragrance: None detected;

Veins: Pinnate; glabrous abaxial and adaxial; midrib about 1.5 mm wide at base, slightly sunken adaxial and raised abaxial;

Vein color: Abaxial midrib between RHS 146D and RHS 145C, adaxial midrib nearest RHS 160B proximally and distally nearest RHS 160A; secondary adaxial and abaxial veins same color as surrounding leaf;

Petiole: Leaves sessile or to about 3.0 mm long and 3.0 mm across; concavo-convex; glabrous;

Petiole color (when present):

Stems: About 30 per plant; terete; stiff; wiry; strong; mostly upright; glabrous; to about 66.0 cm, average about 60.0 cm long and 3.5 mm diameter at base;

Stem color: Nearest RHS 146D;

Nodes: About six per stem below initial flowers; average internode length about 8.0 cm;

Node color: Nearest RHS 145A;

Inflorescence: A loosely-branched compound corymb of about 40 flowers; initial flowering portion about 12.0 cm long and 10.0 cm across;

Flowers: Perfect; salverform with flat face and long fused tube; actinomophic; typically with five petals; about 26.0 mm long total with tube about 25.0 mm long; face about 29.0 mm across; attitude upright to slightly outward; self-cleaning;

Flower longevity: Individually about 5 days on plant or as cut flower;

Flower fragrance: Lightly sweet;

Buds one to two days prior to opening: Narrowly oblanceolate, to nearly clavate; acute apex with petals implicate about each other; base fused; about 27.0 mm long and 2.5 mm diameter in tube and swollen to 3.0 mm diameter toward apex of convolute petals;

Bud color: Petals nearest RHS 85D in bulb and nearest RHS 79D in corolla tube;

Petals: Five; margin entire; apex rounded; base fused into tube; abaxial and adaxial limb glabrous, abaxial tube surface glabrous, adaxial tube glabrous except pubescent in region about 3.0 mm to 5.0 mm from base; limbs imbricate about 25 percent over the next petal;

Petal size: Limb to about 12.0 mm wide and about 13.0 mm long, corolla tube to about 25.0 mm long and 2.5 mm diameter at face;

Petal color: (Young) adaxial limb nearest RHS 76B with two markings about 5.0 mm long at proximal face nearest RHS N80A with white nearest RHS NN155D at proximal center midrib between two longitudinal bands, combining with other petals to form star-like radiated shape; abaxial limb between RHS 76B and RHS 85C; abaxial tube basal 5.0 mm nearest RHS 150D, distally striated with nearest RHS N81B and RHS N81C; adaxial corolla tube nearest RHS 83D with basal 5.0 mm nearest RHS 150D, pubescence nearest RHS NN155D;

Petal color: (Mature) adaxial limb nearest RHS NN155D with faint blush of nearest RHS 84D, center eye with two bands nearest RHS N80B and RHS N155D between the bands; abaxial limb lighter than RHS 84D with center eye blushed lightly nearest RHS NN74D; abaxial corolla tube striated longitudinally nearest RHS 77B and RHS 77C with base nearest RHS NN155D; adaxial throat nearest RHS 77B with basal 5.0 mm nearest RHS NN155B;

Androecium: Five;

*Filaments*.—Typically five; adnate to adaxial corolla tube except free in terminal 1.0 mm; varying lengths between 19.0 mm and 25.0 mm, less than 0.5 mm in diameter; color lighter than RHS 84D.

*Anther*.—Five; oblong elliptic; dorsifixed; longitudinal; about 3.0 mm long by 1.0 mm wide; color nearest RHS 14B.

*Pollen*.—Abundant; color nearest RHS 15A.

Gynoecium: One pistil per flower; to about 25.0 mm long;

*Style*.—Cylindrical; about 22.0 mm long and about 0.3 mm diameter; persistent after flower abscission; color between RHS 150D and RHS 145D.

*Stigma*.—Trifurcate in the distal 1.0 mm, less than 0.25 mm in diameter; color nearest RHS 11A.

*Ovary*.—Superior; conical; acute apex, base truncate; about 2.0 mm long and 1.0 mm diameter; color nearest RHS 144A.

Calyx: Tubular; connate to corolla tube; to about 9.0 mm long and 2.5 mm wide at apex;

Sepals: Five; lanceolate; narrowly acute apex, margin entire; base fused; abaxial surface matte and adaxial slightly lustrous; individually about 9.0 mm long and 1.0 mm wide; fused in basal 5.0 mm to 8.0 mm;

Sepal color: Abaxial variable depending on light exposure, nearest RHS 187C in high light with margins of nearest RHS 186C, in low light exposure nearest RHS 146C with margins of RHS 155A; adaxial nearest RHS 146C with margins nearest RHS 155A;

Peduncle: Glabrous, stiff, strong, moderately lustrous, upright, cylindrical; average about 60.0 cm long and 2.5 mm diameter at base of flower branches and about 3.5 mm diameter near soil; branches to about 28.0 mm long and 2.0 mm diameter at base;

Peduncle color: Nearest RHS 146D;

Pedicel: Cylindrical; micro-glandular; average about 5.0 mm long and 1.0 mm diameter;

Pedicel color: Nearest RHS 146D with moderate blush in heavy light exposure to nearest RHS N186C;

Fruit and seeds have not yet been observed.

Hardiness and culture: The new plant grows best with plenty of moisture and adequate drainage; hardy to at least from USDA zone 4 through 8.

Disease and pest resistance: *Phlox* 'Opening Act Pink-a-Dot' demonstrated the excellent powdery mildew resistance caused by *Erysiphe cichoracearum* in the presence and under conditions of intense pressure that would normally show symptoms.

I claim:

1. A new and distinct cultivar of hybrid *phlox* plant named *Phlox* 'Opening Act Pink-a-Dot', as herein described and illustrated.

* * * * *